US00PP09031P

United States Patent [19]

Saville

[11] Patent Number: Plant 9,031

[45] Date of Patent: Jan. 3, 1995

[54] MINIATURE ROSE PLANT NAMED SAVALAV

[75] Inventor: F. Harmon Saville, Rowley, Mass.

[73] Assignee: Nor'East Miniature Roses, Inc., Rowley, Mass.

[21] Appl. No.: 180,437

[22] Filed: Jan. 12, 1994

[51] Int. Cl.[6] ..... A01H 5/00

[52] U.S. Cl. ..... Plt./9

[58] Field of Search ..... Plt. 7.1, 9

[56] References Cited

U.S. PATENT DOCUMENTS

PP5967 5/1987 Saville ..... Plt./9

*Primary Examiner*—Howard J. Locker

*Attorney, Agent, or Firm*—Christie, Parker & Hale

[57] ABSTRACT

A new miniature rose with soft lavender flowers of good form.

1 Drawing Sheet

SUMMARY OF THE INVENTION

The present invention relates to a new and distinct variety of rose plant of the miniature rose class, which was created by me by crossing as seed parent the variety known as 'Sachet' (also known as 'Savasach'), U.S. Plant Pat. No. 5,967, and as pollen parent the variety known as 'Copper Sunset'. The varietal denomination of this new rose is 'Savalav'.

Among the novel characteristics possessed by this new variety which distinguishes it from its parents and all other varieties of which I am aware is its attractive soft lavender flowers of good form.

Asexual reproduction by propagation of cuttings of the new variety as performed in Essex County, Mass. shows that the foregoing and other distinguishing characteristics come true to form and are established and transmitted through succeeding propagations.

BRIEF DESCRIPTION OF ILLUSTRATION

The accompanying illustration shows typical specimens of the flowers of the new variety in different stages of development depicted in color as nearly true as it is reasonably possible to make the same in a color illustration of this character. Phenotypic expression may vary with light availability, environmental and cultural conditions.

DETAILED DESCRIPTION OF THE NEW VARIETY

The following is a detailed description of my new variety, with color terminology in accordance with the Royal Horticultural Society Colour Chart (RHSCC). The terminology used in color description herein refers to plate numbers in the aforementioned color chart.

Parentage:

*Seed parent.*—'Sachet' also known as 'Savasach' (U.S. Plant Pat. No. 5,967).

*Pollen parent.*—'Copper Sunset' (not patented).

Class: Miniature.

The following observations were made of specimens grown outdoors in Essex County, Mass., during the month of September.

FLOWER

Blooming habit: Recurrent.

A. Bud:

(1) *Size.*—Medium.

(2) *Form.*—Short pointed.

(3) *Color.*—As sepals divide, bud color is near 186B to 186C.

(4) *Sepals.*—Slightly longer than bud, smooth to slightly foliated.

(5) *Peduncle.*—Length — about ¾ inch. Aspect — straight. Strength — erect. Color — near 144A.

B. Bloom:

(1) *Size.*—Average size when fully expanded — about 1¾ to 2 inches.

(2) *Borne.*—Singly and several together in small sprays.

(3) *Form.*—High centered at first becoming flat, petals at first loosely rolled under.

(4) *Petalage.*—Number of petals under normal conditions — about 22-25.

(5) *Color.*—During first two days, inner petals at center of flower near 186C; outer petals near 186C; base of petals at point of attachment near 5D; reverse of petals near 186C and general tonality from a distance soft lavender. As bloom ages the tonality gets lighter, to near 186D.

C. Petals:

(1) *Texture.*—Average.

(2) *Appearance.*—Inside velvety and outside satiny.

(3) *Form.*—Wide fan shape.

(4) *Arrangement.*—Imbricated, regularly arranged, shingle-like.

(5) *Petaloids in center.*—Few.

(6) *Persistence.*—Drop off cleanly.

(7) *Fragrance.*—None to slight.

(8) *Lasting quality.*—Average.

REPRODUCTIVE ORGANS

A. Stamens, Filaments and Anthers:

*Arrangement and color.*—Regularly arranged around styles; color — near 23C.

B. Pollen:

*Color.*—near 23C.

C. Styles: Medium length, thin.

D. Stigmas:

*Color.*—near 4D.

E. Hips: Globular, about ¾ inch, near 24B, seeds do not protrude.

PLANT

A. Form: Compact.

B. Growth: Very vigorous, uniform branching; height attained about 16 inches.

C. Foliage: Compound 5 to 7 leaflets.

(1) *Size.*—Medium.

(2) *Quantity.*—Abundant.

(3) *Color.*—New foliage: Upper side — near 141A, edge 183C. Underside — near 183C. Old foliage: Upper side — near 136A. Underside — near 139B.

(4) *Shape.*—Oval, pointed.

(5) *Texture.*—Upper side is semi-glossy; underside is matte.

(6) *Edge.*—Serrated.

(7) *Serration.*—Even.

(8) *Leaf stem.*—Color — near 139C. Underside — 143C.

(9) *Stipules.*—Medium length, slightly bearded.

(10) *Resistance to disease.*—Blackspot — average. Mildew — average. Rust — average.

D. Wood:

(1) *New wood.*—Color — near 143C to 143B. Bark — smooth.

(2) *Old wood.*—Color — near 200D to 199C. Bark — rough.

E. Thorns:

*Quantity (main stalk).*—Ordinary.

*On laterals from stalk.*—few.

*Form.*—Thin, straight pointed.

*Length.*—Short.

*Color.*—Near 183C.

*Position.*—Irregular.

*Prickles.*—None.

F. Winter Hardiness: Need protection in severe climates.

I claim:

1. A new and distinct variety of rose plant of the miniature rose class, substantially as shown and described.

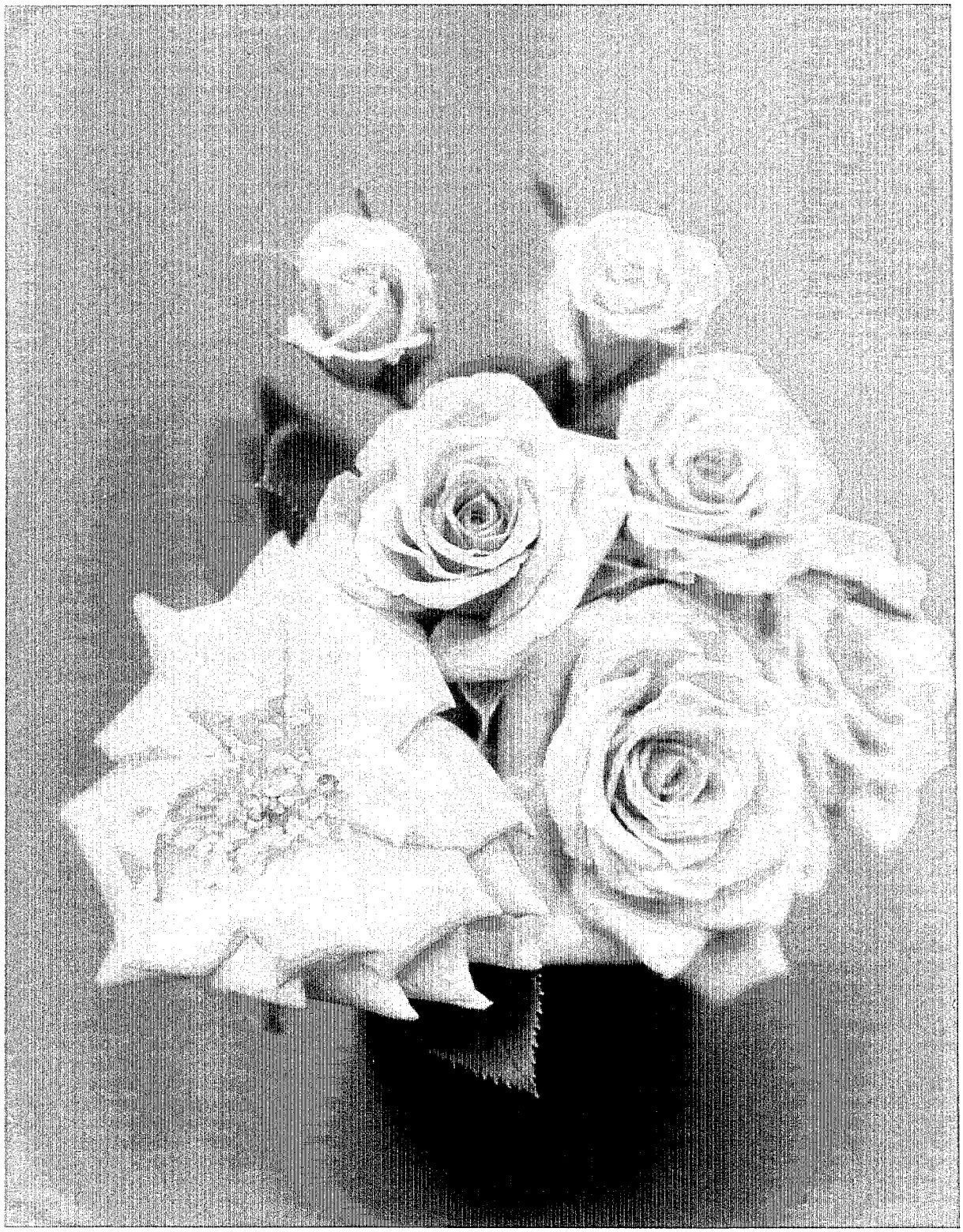

* * * * *